United States Patent [19]
Yamada

[11] Patent Number: 5,902,104
[45] Date of Patent: May 11, 1999

[54] ORTHODONTIC WIRE SUPPORTING DEVICE

[76] Inventor: Kenjiro Yamada, 1-27 Moritsune 1-chome, Kokuraminami-ku Kitakyusyu-shi, Hukuoka-ken, Japan

[21] Appl. No.: 08/980,525

[22] Filed: Dec. 1, 1997

[30] Foreign Application Priority Data

Dec. 4, 1996 [JP] Japan .................................. 8-337651

[51] Int. Cl.$^6$ ....................................................... A61C 3/00
[52] U.S. Cl. .................................................................. 433/8
[58] Field of Search ............................... 433/8, 9, 10, 11, 433/12, 13, 14, 15, 16, 17

[56] References Cited

U.S. PATENT DOCUMENTS

| | | | |
|---|---|---|---|
| 3,765,091 | 10/1973 | Northcutt | 433/9 |
| 3,932,940 | 1/1976 | Andren | 433/9 |
| 4,063,360 | 12/1977 | Waller | 433/9 |
| 4,094,068 | 6/1978 | Schinhammer | 433/9 |
| 4,773,857 | 9/1988 | Herrin | 433/9 X |
| 5,267,854 | 12/1993 | Schmitt | 433/9 X |
| 5,435,720 | 7/1995 | Riebschleger | 433/9 |

*Primary Examiner*—Nicholas D. Lucchesi
*Attorney, Agent, or Firm*—Price, Heneveld, Cooper, DeWitt & Litton

[57] ABSTRACT

An orthodontic wire supporting device, for example, in the form of a bracket improved so that the bracket can be reliably held on teeth during a period of orthodontic treatment but easily detached from teeth, if it is desired, for exchange of the bracket with a fresh one. A base of the bracket destined to be bonded to the tooth plane by means of an adhesive layer is formed adjacent four corners with anchoring holes each defined by a truncated cone having its diameter on the upper side smaller than its diameter on the lower side of the base. The lower side of the base is coated with the adhesive layer, and then the base is pressed against the tooth plane with an appropriate force so that the adhesive layer is partially forced to pass through the respective anchoring holes and to project from the upper side of the base. The portion of the adhesive layer thus projecting from the upper side of the base appropriately bulges to form buttons each having a diameter substantially larger than the diameter of the associated anchoring hole. Once the adhesive layer has been solidified, these buttons come into engagement with the base so as to hold the adhesive layer on the base. Firmly bonding the adhesive layer to the tooth plane allows the bracket to be firmly held on the tooth plane, and cutting off of the buttons facilitates the bracket to be separated from the adhesive layer.

18 Claims, 7 Drawing Sheets

ORTHODONTIC WIRE SUPPORTING DEVICE

BACKGROUND OF THE INVENTION

1. Field of the Invention

This invention relates to an orthodontic wire supporting device such as a bracket adapted to guide a piece of wire placed across selected teeth during an orthodontic treatment.

2. Description of the Related Art

Abnormal occlusion, for example, due to mal-aligned dentition has usually been corrected by so-called orthodontics intending to obtain a normal occlusion by moving mal-aligned teeth to their aligned positions. The orthodontic treatment is carried out by placing a piece of orthodontic wire 1 across selected teeth, as shown by FIG. 9, and then by moving the mal-aligned teeth toward their normally aligned positions under a lateral pressure exerted by the piece of wire 1.

FIG. 9 illustrates a manner of orthodontic treatment. As seen in FIG. 9, wire fixing devices 3 are mounted on first molars 2a, 2b of right and left sides, respectively, and opposite ends of the piece of wire 1 are fixed to the wire fixing devices 3, respectively, so that the piece of wire 1 extends between the first molars 2a, 2b along front sides of premolar and anterior teeth. Sometimes the wire fixing devices are mounted also on second molars 4a, 4b of right and left sides, if necessary to hold the opposite ends of the piece of wire 1 more reliably.

A bracket 6 serving as a wire supporting device adapted to guide the piece of wire 1 is attached to front sides of the teeth to be corrected and the piece of wire 1 is guided by this bracket 6 between the first molars 2a, 2b. The respective teeth necessarily shift more or less as the orthodontic treatment progresses. Accordingly, it is essential to hold the piece of wire 1 slidably relative to the bracket 6 without any apprehension that the piece of wire 1 might unintentionally fall off from the bracket 6. The opposite ends of the piece of wire 1 define reference positions for the orthodontic treatment. Accordingly, it is important that the opposite ends are fixed on the respective wire fixing devices with a sufficient stability to prevent the piece of wire 1 from slipping out of place relative to the first molars 2a, 2b. Simultaneously, it is also important that the wire fixing devices 3 are fixed on the first molars 2a, 2b with a sufficient stability to prevent the devices 3 from unintentionally falling off.

While the wire fixing devices 3 are firmly bonded to the first molars 2a, 2b (sometimes also to the second molars), the bracket 6 must be attached to each tooth so that the bracket 6 can be easily detached from the tooth when it is desired. More specifically to describe, the tooth necessarily shifts as the treatment progresses and, at the position thus shifted, the piece of wire 1 cannot be properly guided by the bracket 6. In this case, the bracket 6 must be detached from the tooth in order to be exchanged with a fresh one. The bracket 6 must be detached also upon completion of the treatment. So long as the piece of wire 1 is being guided by the bracket 6, it would be inconvenient for the treatment that the bracket 6 might fall off from the tooth. Accordingly, the bracket 6 must be properly bonded to the tooth.

FIG. 8 is a perspective view schematically showing a configuration of the conventional bracket 6. This bracket 6 comprises a substantially rectangular base 61 destined to be bonded to the teeth, a bridge-like portion 62 integrally rising from the base 61 in the middle thereof and a guide groove 63 formed in a top of the bridge-like portion 62 in the middle thereof so as to receive the piece of wire 1.

As has been described above, it is required for the bracket 6 to be reliably held on the front side of the tooth so long as the piece of wire 1 is being guided by the bracket 6. It is also required for the bracket 6 to be easily detached from the tooth in view of the fact that the bracket 6 must be often exchanged with a fresh one as the treatment progresses. However, with the above-mentioned bracket 6 of the prior art, it depends on an adhesive effect of used adhesive agent whether the bracket 6 can be easily detached from the tooth or not, since the bracket 6 is usually bonded to the tooth by means of adhesive coating the base 61 of this bracket 6. Use of an adhesive agent presenting a relatively high adhesive effect certainly assures that the bracket 6 is firmly held on the tooth during the orthodontic treatment. However, use of such adhesive agent will make it difficult to detach the bracket 6 from the tooth, for example, when it is desired to exchange the bracket with a fresh one and correspondingly will make the operation of exchange troublesome. Use of an adhesive agent tending to facilitate the operation of exchange may cause the bracket 6 to fall off during the treatment and make the desired treatment impossible. Additionally, it is required for a dentist to select the most suitable adhesive agent from various types of adhesive agents depending on the particular material of the bracket 6 and this is a burden which is not negligible for the dentist.

SUMMARY OF THE INVENTION

In view of the problem as has been described above, it is a principle object of the invention to provide an orthodontic wire supporting device adapted to be attached to the tooth plane without entirely relying upon an effect of adhesive agent so that the device may be reliably held on the tooth plane during a period of orthodontic treatment, but easily detached from the tooth plane for exchange of the device with a fresh one or upon completion of the treatment.

The object set forth above is achieved, according to the invention, by an orthodontic wire supporting device adapted to be bonded to the tooth plane by means of an adhesive layer and thereby to support a piece of orthodontic wire placed across selected teeth. The orthodontic wire supporting device including a base of the device destined to be bonded to the tooth plane is formed with an appropriate number of anchoring guides; and a portion of the adhesive layer applied on a lower side of the base is forced to pass through the anchoring guides until forward ends of the portion passing through the anchoring guides project from an upper side of the base.

These and other features, objects, and benefits of the invention will be recognized by those who practice the invention and by those skilled in the art, from reading the following specification and claims, together with reference to the accompanying drawings.

DETAILED DESCRIPTION OF THE EMBODIMENTS

Details of the inventive device used to support and guide the orthodontic wire will be more fully understood from the description of preferred embodiments given hereunder in reference with the accompanying drawings. As a specific wire supporting device, the bracket is adapted to support and guide as will be illustrated and described.

Figure 1:
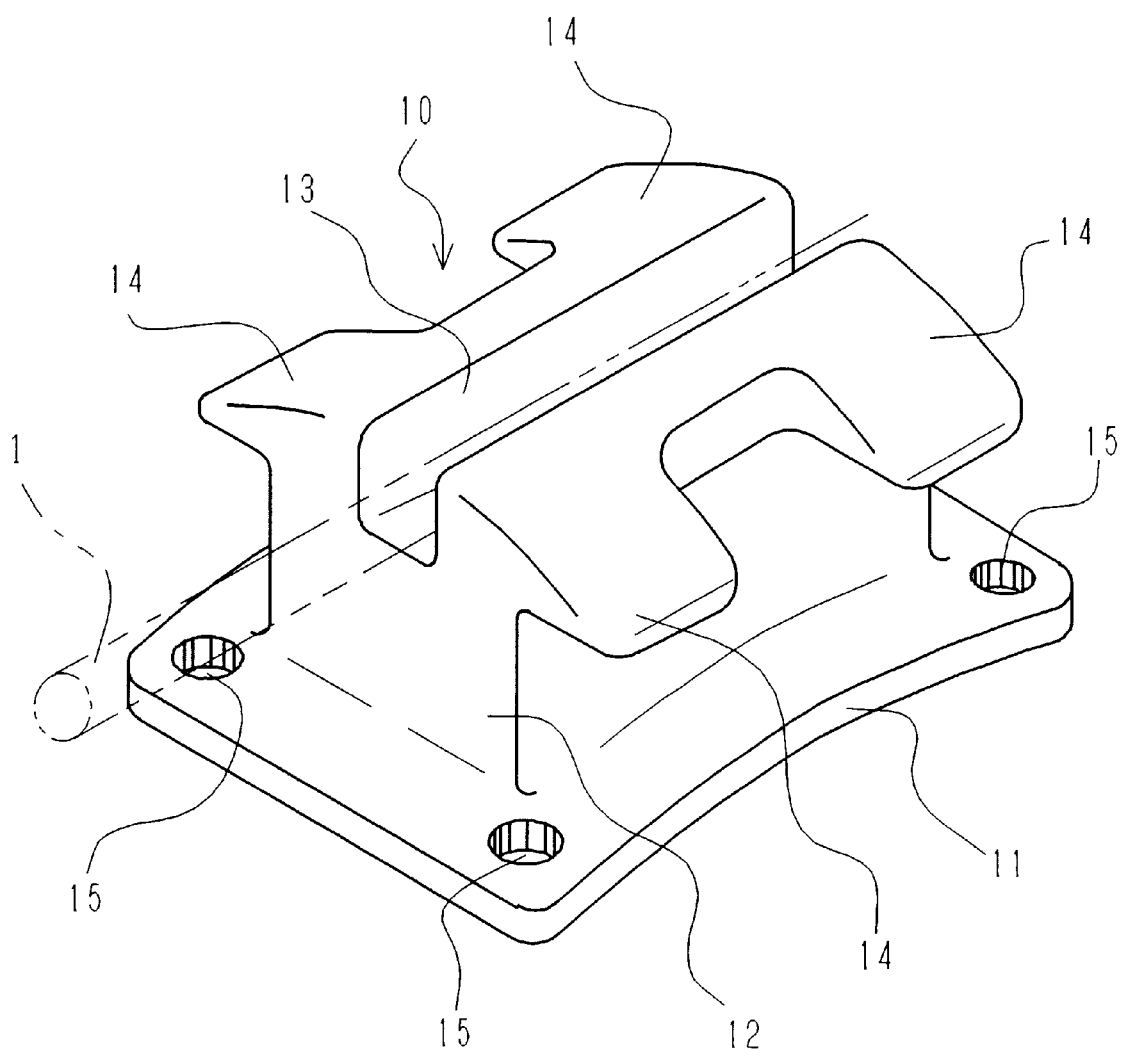
FIG. 1 is a perspective view of a novel bracket serving as a device to support and guide orthodontic wire.

FIG. 1 is a perspective view schematically showing a bracket 10 as the wire guiding device configured according to the invention. As shown, the bracket 10 comprises a substantially rectangular base 11, a bridge-like portion 12 rising from the base 11 in the middle thereof and having an appropriate width, and a guide groove 13 formed in the top of the bridge-like portion 12 to receive and guide a piece of wire 1. As will be apparent from FIG. 3, the base 11 is somewhat curved in the direction of the guide groove 13 so as to extend along a tooth plane. In addition to the guide groove 13, the top of the bridge-like portion 12 is provided with two pairs of guide wings 14 each extending outward from the bridge-like portion 12 in opposite directions orthogonally to the guide groove 13. Surfaces of these guide wings 14 are appropriately curved transversely of the guide groove 13 so that the piece of wire 1 under an appropriate tension may be slidably moved along the surfaces toward the guide groove 13 so as to be received by the guide groove 13. The base 11, the bridge-like portion 12, and the guide wings 14 of this bracket 10 are integrally molded from stainless steel, synthetic resin, or ceramics such as polycrystal- or single-crystal alumina or zirconium oxide.

Figure 2:
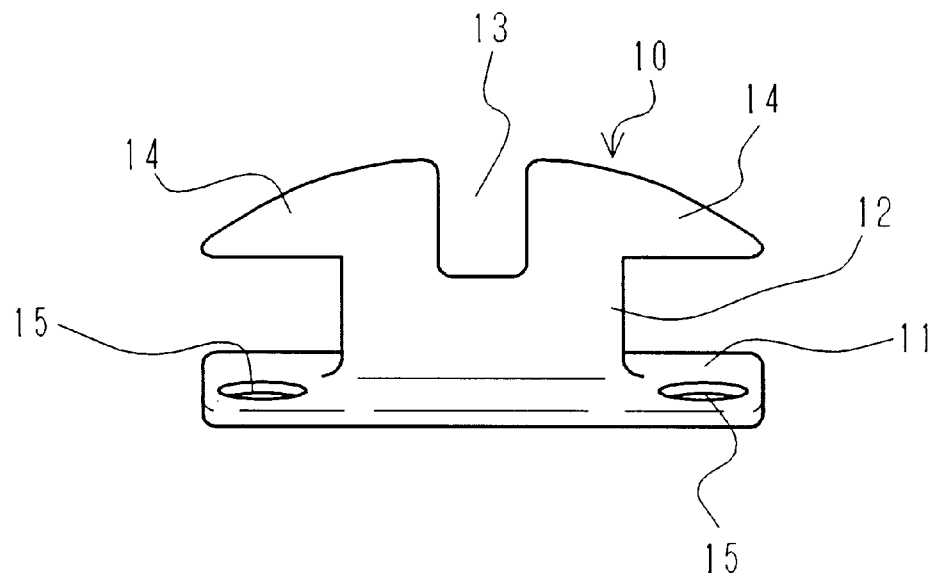
FIG. 2 is a side view of the novel bracket serving as a device to support and guide the orthodontic wire.
Figure 3:
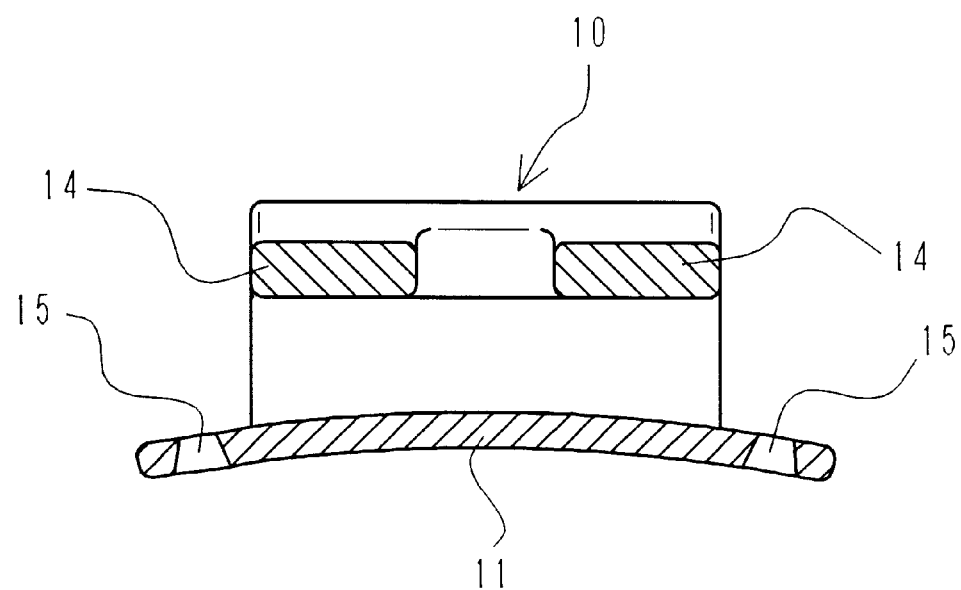
FIG. 3 is a sectional view of the novel bracket serving as a device to support and guide the orthodontic wire taken along line A—A in FIG. 5.

As will be seen in FIGS. 1–3, the base 11 of the bracket 10 is formed at its four corners with anchoring guides in the form of through-holes 15 extending through base 11 in the direction of thickness. Each of these anchoring holes 15 is tapered, as will be apparent from FIG. 3, so that its diameter on the upper side is smaller than its diameter on the lower side of the base 11 and its inner wall defines a truncate cone. While the anchoring holes 15 are herein illustrated and described as being formed at the four corners of the base 11, the locations as well as the number of these anchoring holes 15 are not limited to those adopted by the illustrated embodiment. Specifically, it is also possible without departing from the spirit and the scope of the invention to form them at two locations or at four locations, i.e., in the middle of the respective sides defining the rectangular or at six locations, i.e., in the middle of a pair of opposite sides and four corners of the rectangle, depending on the size of the base 11.

Figure 6:
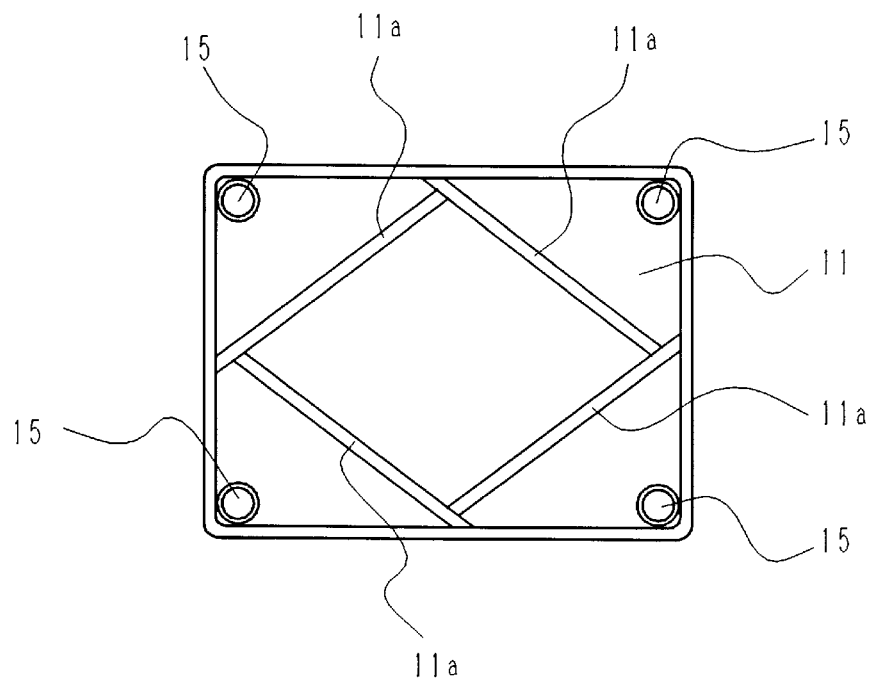
FIG. 6 is a rear view of the novel bracket serving as a device to support and guide the orthodontic wire.

As shown in FIG. 6, the lower side of the base 11 is formed with projections of selective configuration in order to adjust an adhesion force of adhesive applied on the lower side so that the base 11 may be prevented from being readily displaced or from being unintentionally separated from the tooth plane, but the base 11 should not be too firmly bonded to the tooth plane.

Figure 4:
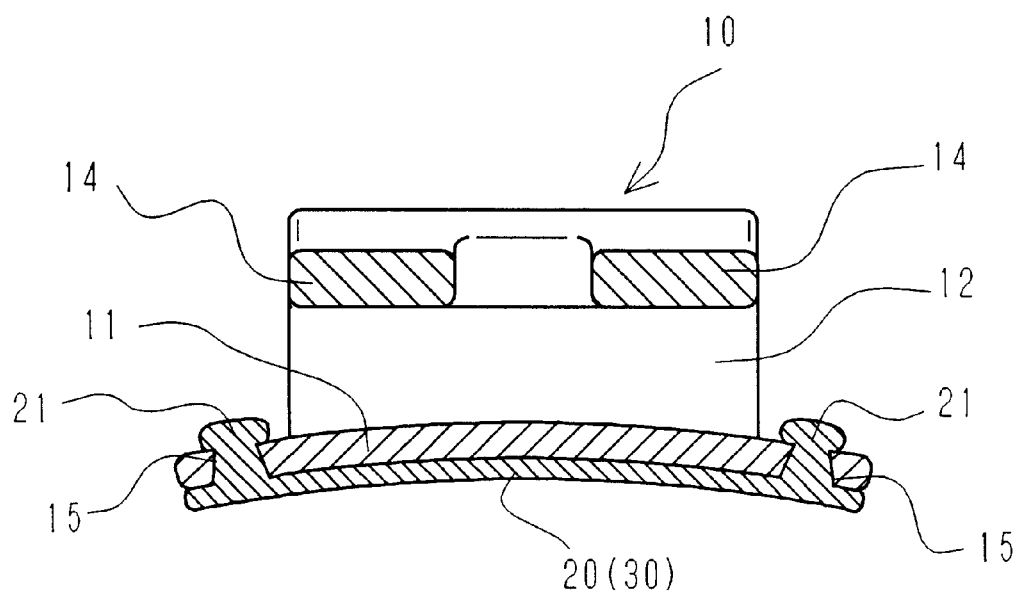
FIG. 4 is a view similar to FIG. 3 showing the novel bracket serving as a device to support and guide the orthodontic wire but as having been applied with adhesive.
Figure 5:
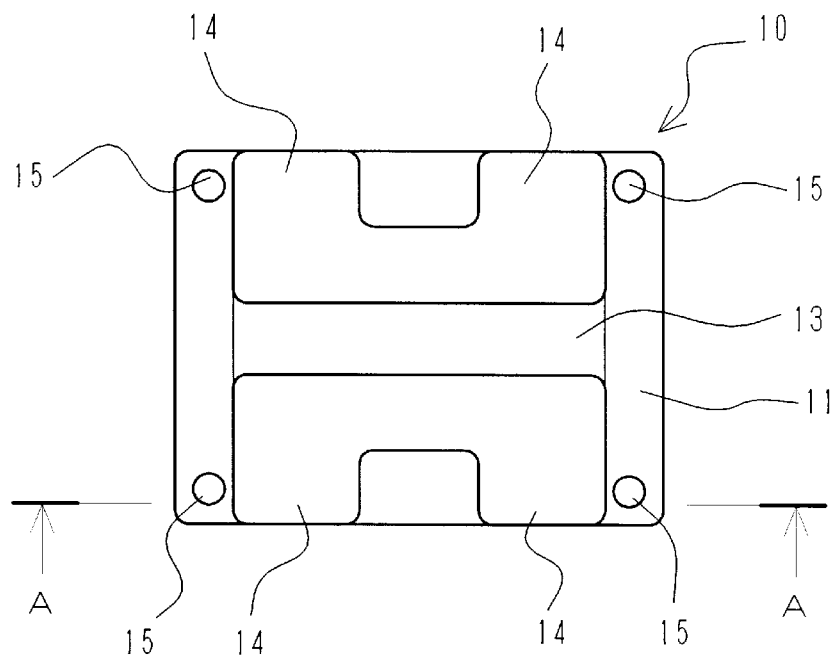
FIG. 5 is a front view of the novel bracket serving as a device to support and guide the orthodontic wire.

FIG. 4 shows the bracket 10 after the lower side of the base 11 has been coated with an adhesive layer 20. The adhesive layer 20 thus coating the lower side partially flows through the anchoring holes 15 and bulges out on the upper side of the base 11. The bulging portions of the adhesive layer 20 form buttons 21 each having a diameter larger than the inner diameter of the associated anchoring hole 15.

The supporting device for orthodontic wire according to the invention as has been described hereinabove with respect to the specific embodiment thereof operates in a manner more fully described below.

Referring to FIG. 4, operation of bonding the bracket 10 to the tooth plane is carried out by coating the lower side of the base 11 with the adhesive layer 20 and then pressing the adhesive layer 20 against the base 11 with an appropriate force. The adhesive layer 20 is partially forced thereby to flow through the anchoring holes 15 until forward ends of these adhesive flows thus passing through the respective anchoring holes 15 project from the upper side of the base 11. The portions of the adhesive layer 20 exposed on the upper side of the base 11 freely bulge, as they are released from the pressing effect, to form buttons 21 each having a diameter larger than that of the associated anchoring hole 15 as seen in FIG. 4. Once the adhesive layer 20 has been solidified, these buttons 21 come in engagement with peripheral edges of the respective anchoring holes 15 on the upper side of the base 11 so as to hold a solidified layer of adhesive 20 on the base 11. In order words, the bracket 10 coated with the adhesive layer 20 may be pressed against the tooth plane before the adhesive layer 20 is solidified to attach the bracket 10 to the tooth plane with the adhesive layer 20 appropriately solidified. It should be understood here that the operation of bonding the bracket 10 to the tooth plane must be carried out simultaneously with operation of introducing the piece of wire 1 into the guide groove 13 of the bracket 10. The bracket 10 is firmly bonded to the tooth plane as the adhesive layer 20 is further solidified and thus unintentional separation between the adhesive layer 20 and the bracket 10 is reliably prevented by engagement of the buttons 21 with the upper side of the base 11.

Detachment of the bracket 10 from the tooth plane is achieved by scraping off of the buttons 21. Once the buttons 21 have been scraped off, there is no more engagement of the solidified adhesive layer 20 with the base 11 of the bracket 10. Consequently, it becomes possible to separate the bracket 10 from the solidified adhesive layer 20. The inner walls of the respective anchoring holes 15 preferably define truncated cones each being tapered toward the upper side of the base 11 so that the bracket 10 may be easily separated from the solidified adhesive layer 20. Residual amount of the adhesive layer on the tooth plane may be removed by scraping this off from the tooth plane.

It is also possible to perform a base layer for adhesion 30 including the buttons 21 on the lower side of the base 11 and then to bond this base layer 30 to the tooth plane. The base layer for adhesion 30 corresponds to the adhesive layer 20 in FIG. 4, and the base layer for adhesion 30 is firmly held on the base 11 by engagement of the buttons 21 making a part of the base layer for adhesion 30 with the base 11. This base layer for adhesion 30 is coated with suitable adhesive by means of which the bracket 10 is bonded to the tooth plane. The base layer for adhesion 30 may be formed by, for example, resinous material having no adhesive property, or by suitable adhesive. The base layer for adhesion formed by suitable adhesive will allow the base layer for adhesion 30 to be easily bonded to the base 11 and, in addition, facilitate formation of the buttons 21 as in the previously mentioned embodiment. The bracket 10 previously formed with the base layer for adhesion 30 allows the buttons 21 to be reliably formed in advance and correspondingly reduces time and labor required to bond the bracket 10 to the tooth plane.

Scraping off of the buttons 21 formed by a part of the base layer for adhesion 30 facilitates the bracket 10 to be detached from the base layer for adhesion 30. Detachment of the bracket 10 is completed by scraping off of the residual amount of adhesive and the base layer for adhesion 30 from the tooth plane.

With the orthodontic wire supporting device of the invention, engagement of the wire supporting device with the adhesive layer 20 or the base layer for adhesion 30 is essentially achieved by engagement of the buttons 21 formed by a portion of the adhesive layer 20 or base layer for adhesion 30 which has been forced to pass through the respective anchoring holes 15 of the base 11 with the wire supporting device. Accordingly, it is not required that the adhesive layer 20 or base layer for adhesion 30 should be firmly bonded to the wire supporting device, and it is rather preferable that the adhesive layer 20 or base layer for adhesion 30 can be easily separated from the wire supporting device. So far as the adhesive layer 20 or the adhesive layer with which the base layer for adhesion 30 is coated is firmly bonded to the tooth plane but not to the wire supporting device, it is unnecessary to select any particular type of adhesive depending on material or the other characterizing factors of the wire supporting device.

Figure 7:
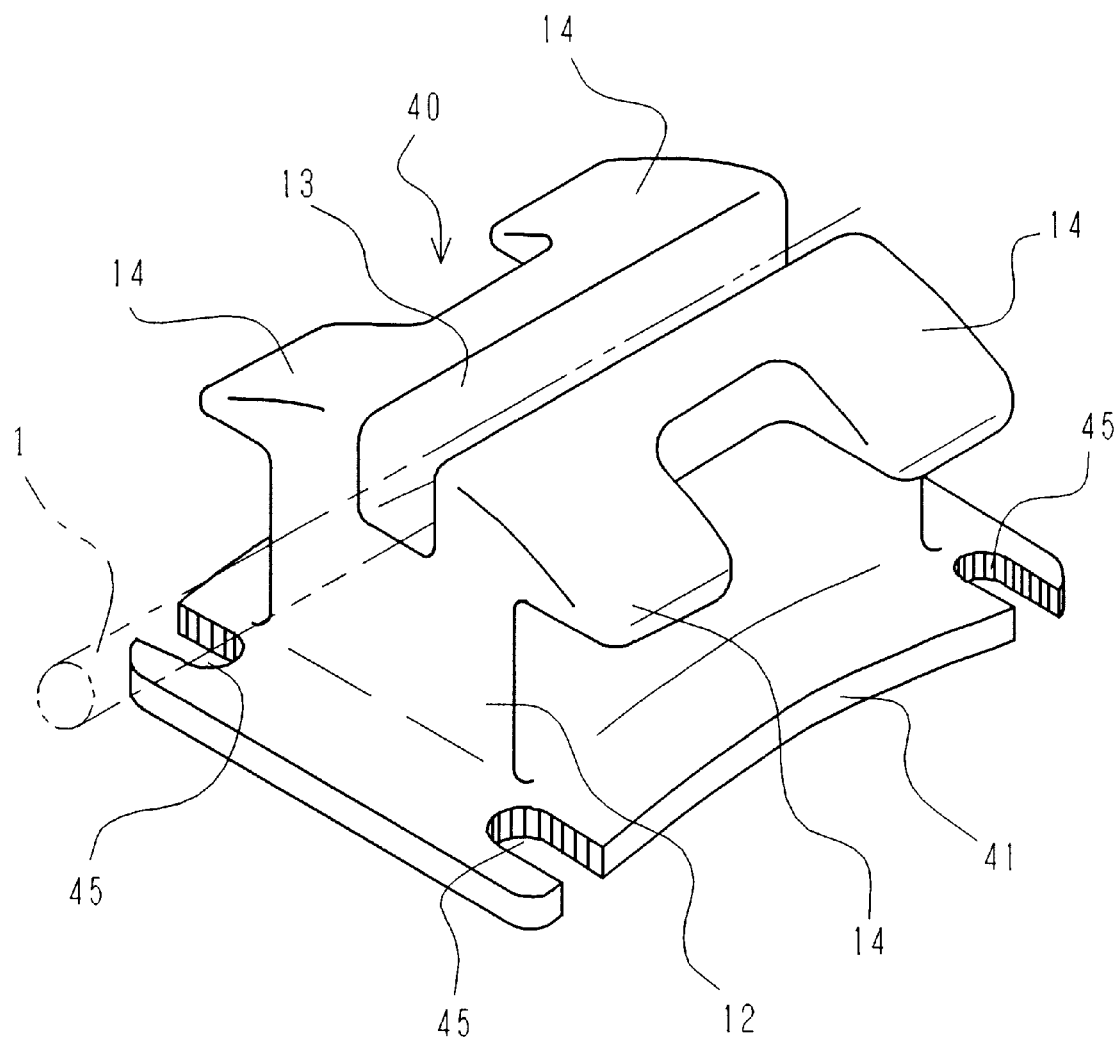
FIG. 7 is a view similar to FIG. 1 showing an alternative embodiment of the bracket serving as a device to support and guide the orthodontic wire.
Figure 8:
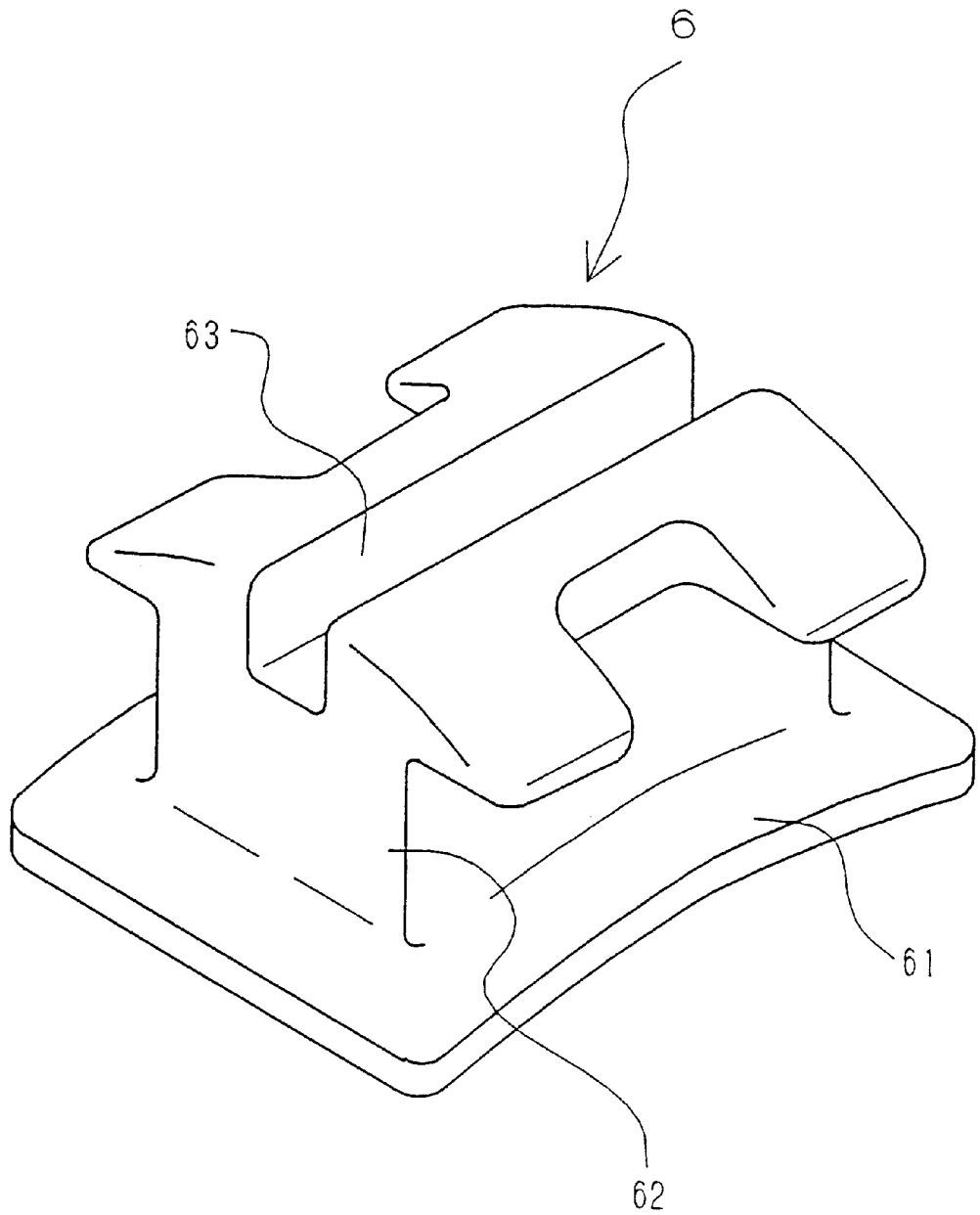
FIG. 8 is a view similar to FIG. 1 schematically showing the bracket of well-known art.
Figure 9:
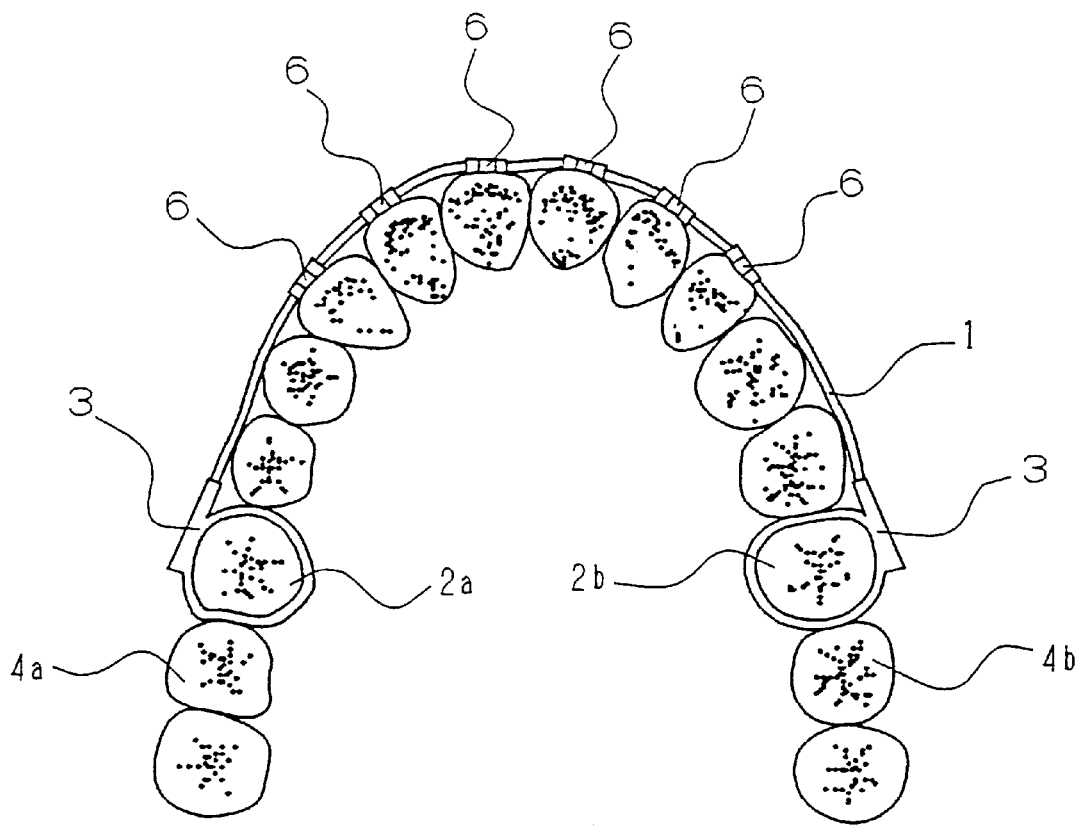
FIG. 9 is a plan view of a dentition illustrating a manner in which the orthodontic treatment is performed.

FIG. 7 is a perspective view showing a bracket 40 according to an alternative embodiment of the invention, in which the parts similar to those in the embodiment shown by FIG. 1 are designated by the similar reference numerals, respectively. A base 41 of this bracket 40 is formed adjacent each corner with a notch 45 of an appropriate length extending inward from transversely opposite side edges of the base 41 so that the notch 45 may serve as an anchoring guide. Specifically, the adhesive layer 20 is partially forced to pass along these notches 45 and to project from the upper side of the base 41 as the lower side of the base 41 is coated with the adhesive layer 20 and then pressed against the tooth plane. The portion thus projecting from the upper side of the base 41 is then solidified to form the bulges corresponding to the previously mentioned buttons 21 which come in engagement with the upper side of the base 41. In this manner, engagement of the adhesive layer 20 with the upper side of the base 41 prevents these two components from readily separating from each other.

In this alternative embodiment shown by FIG. 7, each notch 45 is preferably configured to that a width thereof on the upper side is smaller than that on the lower side of the base 41 and an inner wall of said notch 45 obliquely extends. Such configuration of the notches advantageously facilitates the bracket 40 to be detached from the tooth plane, when it is desired, without any significant resistance.

While the wire supporting device according to the invention has been described hereinabove as comprising the bracket 10 or 40 serving also as the wire guiding device, it should be understood that the invention is applicable also to a wire fixing device.

Accordingly, the present invention provides an orthodontic wire supporting device adapted to be bonded to the tooth plane by means of an adhesive layer and thereby to support a piece of orthodontic wire placed across selected teeth. The orthodontic wire supporting device includes a base of the device destined to be bonded to the tooth plane formed with an appropriate number of anchoring guides. A portion of the adhesive layer applied on the lower side of the base is forced to pass through the anchoring guides until forward ends of the portion passing through the anchoring guides project from an upper side of the base.

The portion of the adhesive layer having passed through the anchoring guides and projected from the upper side of the base bulges beyond peripheral edges of the respective anchoring guides as the adhesive layer is solidified. These bulges come in engagement with the base and thereby prevent the adhesive layer applied on the lower side of the base from unintentionally separating from the base. Accordingly, the wire supporting device can be reliably held on the tooth plane so far as an adhesive agent having a sufficiently high adhesion force to be firmly bonded to the tooth plane is selected to form the adhesive layer.

When it is desired to detach the wire supporting device from the tooth plane, for example, in order to exchange the device with a fresh one, the portion of the solidified adhesive layer projecting from the upper side of the base may be scraped off. As a consequence, no portion of the adhesive layer remains in engagement with the upper side of the base, and the wire supporting device can be easily detached from the tooth plane by separating the device from the adhesive layer. It is possible, therefore, to avoid an excessively firm bonding between the adhesive layer and the wire supporting device and thereby to facilitate the operation of scraping the residual adhesive layer off from the tooth plane.

As has been described above, it is the important feature of the invention to bond the adhesive layer to the wire supporting device essentially by the portion of the solidified adhesive layer projecting from the upper side of the base and the wire supporting device can be easily detached from the tooth plane by scraping the projecting portion of the adhesive layer off from the base. According to this principle, it is also possible to perform the lower side of the base with a base layer for adhesion having a portion extending through the anchoring guides and projecting from the upper side of this base layer for adhesion so as to come in engagement with the upper side of the wire supporting device's base and to bond such base layer for adhesion to the tooth plane by means of suitable adhesive. In the case of the wire supporting device without being formed with such base layer of adhesion, there is an apprehension that, when the wire supporting device coated with the adhesive layer is pressed against the tooth plane, no portion of the adhesive layer might project from the upper side of the base sufficiently to come in engagement with the wire supporting device. This apprehension can be reliably avoided by performing the base layer for adhesion by which the wire supporting device is bonded to the tooth plane. In view of such fact, the invention also provides an orthodontic wire supporting device adapted to be bonded to tooth plane by means of an adhesive layer and thereby to support a piece of orthodontic wire placed across selected teeth, the orthodontic wire supporting device being characterized by that a base of the device destined to be bonded to the tooth plane is formed with an appropriate number of anchoring guides; the base is formed on its lower side with a base layer for adhesion; and the base layer for adhesion partially extends through the anchoring guides until forward ends thereof project from an upper side of the base so as to come in engagement with the upper side of the base.

To bond this wire supporting device to the tooth plane, the base layer for adhesion may be coated with the adhesive layer by means of which the device is bonded to the tooth plane. To detach the wire supporting device from the tooth plane, the portion of the base layer for adhesion projecting from the upper side of the base may be scraped off and then the wire supporting device may be separated from the base layer for adhesion.

As has already been described, no firm bonding is necessary between the wire supporting device and the adhesive layer or the base layer for adhesion. However, it should be avoided that the wire supporting device might slip out of place relative to the adhesive layer or the base layer for adhesion. From this viewpoint, the lower side of the base is appropriately formed with irregularities in order to prevent the adhesive layer or the base layer for adhesion from slipping out of place relative to the lower side of the base.

The anchoring guides must serve to guide a portion of the adhesive layer coating the lower side of the base or the base layer for adhesion until such portion projects from the upper side of the base and laterally bulges. To achieve this, the anchoring guides preferably comprise through-holes extending through the base in the direction of thickness or comprise notches cut inward from a pair of opposite sides of the base.

With the wire supporting device having the anchoring guides comprising the through-holes, inner walls of the through-holes respectively define truncate cones each being tapered so that its diameter on the upper side is smaller than that on the lower side of the base. With the wire supporting device having the anchoring guides comprising the notches, each of the notches is defined by an inner wall slanted so that each of the notches has a width on the upper side smaller than that on the lower side of the base.

After the portion of the adhesive layer or the base layer for adhesion projecting from the upper side of the base has been scraped off, the slanted inner walls of the respective through-holes or anchoring notches allow the base to be separated from the adhesive layer or the base layer for adhesion which is bonded to the tooth plane without any significant resistance to thereby allow the wire supporting device to be easily detached from the tooth plane.

To hold the wire supporting device evenly on the tooth plane and thereby to achieve a reliable wire guiding effect, the anchoring guides are provided preferably adjacent respective corners of the base which is substantially rectangular.

In view of a fact that the wire guiding device is more frequently exchanged with a fresh one than the wire fixing device during orthodontic treatment, the wire supporting device preferably functions also as a wire guiding device.

Although not so frequent as in the case of the wire guiding device, the wire fixing device must be exchanged with a fresh one to compensate a slipping out of place relative to the tooth plane. To facilitate it, the wire supporting device preferably functions also as a wire fixing device.

As will be apparent from the foregoing description, the orthodontic wire supporting device according to the invention can be reliably held on the tooth plane during the orthodontic treatment by assuring a firm bonding between the tooth plane and the adhesive layer. This is achieved by a feature of the invention, such that a portion of the adhesive layer applied on the lower side of the base is forced to pass through the anchoring holes or notches formed in the base until the forward ends of the portion passing through the anchoring holes or notches project from the upper side of the base and laterally bulge beyond the peripheral edges of the respective anchoring holes or notches. Once the adhesive layer has been solidified, these bulges come into engagement with the base, on one hand, and the adhesive layer is bonded to the wire supporting device as well as to the tooth plane. Additionally, the invention allows the wire supporting device not only to be easily separated from the adhesive layer but also to be conveniently exchanged with the fresh one.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

The embodiments of the invention in which an exclusive property or privilege is claimed are defined as follows:

1. An orthodontic wire supporting device adapted to be bonded to a tooth plane by means of an adhesive layer and thereby to support a piece of orthodontic wire placed across selected teeth, said orthodontic wire supporting device comprising:
    a base destined to be bonded to the tooth plane formed with an appropriate number of anchoring guides;
    a portion of an adhesive layer applied on a lower side of said base adapted to be forced to pass through said anchoring guides until forward ends of said portion passing through said anchoring guides project from an upper side of said base; and
    means for removing said device from said adhesive layer comprising
        a button section for engaging with an edge of said anchoring guides wherein said orthodontic wire supporting device is removed from said adhesive layer by cutting said button section.

2. The orthodontic wire supporting device according to claim 1, wherein said lower side of said base is formed with irregularities in order to prevent said adhesive layer applied on said lower side from slipping out of place relative to said lower side of said base.

3. The orthodontic wire supporting device according to claim 1, wherein said anchoring guides comprise through-holes extending through said base in a direction of thickness.

4. The orthodontic wire supporting device according to claim 1, wherein said anchoring guides comprise notches cut inward from a pair of opposite sides of said base.

5. The orthodontic wire supporting device according to claim 1, wherein said anchoring guides are provided adjacent respective corners of said base which is substantially rectangular.

6. The orthodontic wire supporting device according to claim 1, wherein said wire supporting device functions also as a wire guiding device.

7. The orthodontic wire supporting device according to claim 1, wherein said wire supporting device functions also as a wire fixing device.

8. An orthodontic wire supporting device adapted to be bonded to a tooth plane by means of an adhesive layer and thereby to support a piece of orthodontic wire placed across selected teeth, said orthodontic wire supporting device comprising:
    a base destined to be bonded to the tooth plane formed with an appropriate number of anchoring guides;
    said base formed on its lower side with a base layer for adhesion;
    said base layer for adhesion partially extends through said anchoring guides until forward ends thereof project from an upper side of said base so as to come into engagement with said upper side of said base; and
    means for removing said device from said adhesive layer comprising a button section for engaging with an edge of said anchoring guides wherein said orthodontic wire supporting device is removed from said base layer for adhesion by cutting said button section.

9. The orthodontic wire supporting device according to claim 8, wherein said lower side of said base is formed with irregularities in order to prevent said base layer for adhesion from slipping out of place relative to said lower side of said base.

10. The orthodontic wire supporting device according to claim 8, wherein said anchoring guides comprise through-holes extending through said base in a direction of thickness.

11. The orthodontic wire supporting device according to claim 8, wherein said anchoring guides comprise notches cut inward from a pair of opposite sides of said base.

12. The orthodontic wire supporting device according to claim 8, wherein said anchoring guides are provided adjacent respective corners of said base which is substantially rectangular.

13. The orthodontic wire supporting device according to claim 8, wherein said wire supporting device functions also as a wire guiding device.

14. The orthodontic wire supporting device according to claim 8, wherein said wire supporting device functions also as a wire fixing device.

15. An orthodontic wire supporting device adapted to be bonded to a tooth plane by means of an adhesive layer and thereby to support a piece of orthodontic wire placed across selected teeth, said orthodontic wire supporting device comprising:
  a base destined to be bonded to the tooth plane formed with an appropriate number of anchoring guides; and
  a portion of an adhesive layer applied on a lower side of said base adapted to be forced to pass through said anchoring guides until forward ends of said portion passing through said anchoring guides project from an upper side of said base, wherein said anchoring guides comprise through-holes extending through said base in a direction of thickness, and inner walls of said through-holes respectively define truncate cones each being tapered so that its diameter on the upper side is smaller than that on the lower side of the base.

16. An orthodontic wire supporting device adapted to be bonded to a tooth plane by means of an adhesive layer and thereby to support a piece of orthodontic wire placed across selected teeth, said orthodontic wire supporting device comprising:
  a base destined to be bonded to the tooth plane formed with an appropriate number of anchoring guides; and
  a portion of an adhesive layer applied on a lower side of said base adapted to be forced to pass through said anchoring guides until forward ends of said portion passing through said anchoring guides project from an upper side of said base, wherein said anchoring guides comprise notches cut inward from a pair of opposite sides of said base, and each of said notches is defined by an inner wall slanted so that each of said notches has a width on the upper side smaller than on the lower side of the base.

17. An orthodontic wire supporting device adapted to be bonded to a tooth plane by means of an adhesive layer and thereby to support a piece of orthodontic wire placed across selected teeth, said orthodontic wire supporting device comprising:
  a base destined to be bonded to the tooth plane formed with an appropriate number of anchoring guides;
  said base formed on its lower side with a base layer for adhesion; and
  said base layer for adhesion partially extends through said anchoring guides until forward ends thereof project from an upper side of said base so as to come into engagement with said upper side of said base, wherein said anchoring guides comprise through-holes extending through said base in a direction of thickness, and inner walls of said through-holes respectively define truncate cones each being tapered so that its diameter on the upper side is smaller than that on the lower side of the base.

18. An orthodontic wire supporting device adapted to be bonded to a tooth plane by means of an adhesive layer and thereby to support a piece of orthodontic wire placed across selected teeth, said orthodontic wire supporting device comprising:
  a base destined to be bonded to the tooth plane formed with an appropriate number of anchoring guides;
  said base formed on its lower side with a base layer for adhesion; and
  said base layer for adhesion partially extends through said anchoring guides until forward ends thereof project from an upper side of said base so as to come into engagement with said upper side of said base, wherein said anchoring guides comprise notches cut inward from a pair of opposite sides of said base, and each of said notches is defined by an inner wall slanted so that each of said notches has a width on the upper side smaller than that on the lower side of the base.

* * * * *

UNITED STATES PATENT AND TRADEMARK OFFICE
CERTIFICATE OF CORRECTION

PATENT NO.   :  5,902,104
DATED        :  May 11, 1999
INVENTOR     :  Kenjiro Yamada It is certified that error appears in the above-identified patent and that said Letters Patent is hereby corrected as shown below:

Abstract, line 6;
    Delete "means".

Column 3, line 45;
    "comers" should be --corners--.

Column 9, claim 12, line 18;
    "comers" should be --corners--.

Signed and Sealed this

Seventh Day of December, 1999

Attest:

Attesting Officer

Q. TODD DICKINSON

Acting Commissioner of Patents and Trademarks